(12) United States Patent
Yoon et al.

(10) Patent No.: US 10,809,127 B2
(45) Date of Patent: Oct. 20, 2020

(54) METHOD AND APPARATUS FOR ANALYZING SPECTRAL INFORMATION

(71) Applicant: SAMSUNG ELECTRONICS CO., LTD., Suwon-si (KR)

(72) Inventors: Youngzoon Yoon, Hwaseong-si (KR); Hyochul Kim, Yongin-si (KR); Younggeun Roh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/376,799

(22) Filed: Apr. 5, 2019

(65) Prior Publication Data

US 2020/0116567 A1    Apr. 16, 2020

(30) Foreign Application Priority Data

Oct. 10, 2018  (KR) .......................... 10-2018-0120614

(51) Int. Cl.
*G01J 3/28* (2006.01)
*G01J 3/02* (2006.01)
(Continued)

(52) U.S. Cl.
CPC .......... *G01J 3/2823* (2013.01); *G01J 3/0205* (2013.01); *A61B 5/1455* (2013.01);
(Continued)

(58) Field of Classification Search
CPC .................. G01J 3/2823; G01J 3/0205; G01J 2003/2826; G01J 2003/283; G01J 2003/2833; A61B 5/14532; A61B 5/1455
See application file for complete search history.

(56) References Cited

U.S. PATENT DOCUMENTS

2013/0297254 A1*  11/2013  Vignesh ................. G01N 21/65
                                                        702/179
2015/0305658 A1*  10/2015  Islam .................... G01N 21/35
                                                         433/27
(Continued)

FOREIGN PATENT DOCUMENTS

KR  10-1560721 B1  10/2015
KR  10-1640202 B1   7/2016
KR  10-1670433 B1  10/2016

OTHER PUBLICATIONS

Jie Bao et al. "A colloidal Quantum dot spectrometer", Nature, vol. 523, Jul. 2, 2015. (16 pages total).

(Continued)

*Primary Examiner* — Tarifur R Chowdhury
*Assistant Examiner* — Jonathon Cook
(74) *Attorney, Agent, or Firm* — Sughrue Mion, PLLC

(57) ABSTRACT

An apparatus for analyzing spectral information includes a database configured to store spectral information of a plurality of materials analyzed by the apparatus, a spectroscopic unit configured to generate spectral information of a subject by filtering an optical signal received from the subject in units of wavelengths, and a controller configured to obtain correlations between spectral information of each of candidate materials from among the plurality of materials and the spectral information of the subject, and generate result information based on the correlations.

16 Claims, 15 Drawing Sheets

(51) Int. Cl.
  *A61B 5/1455* (2006.01)
  *A61B 5/145* (2006.01)
(52) U.S. Cl.
  CPC ... *A61B 5/14532* (2013.01); *G01J 2003/2826* (2013.01); *G01J 2003/2833* (2013.01)

(56) References Cited

U.S. PATENT DOCUMENTS

| | | | |
|---|---|---|---|
| 2016/0025569 A1* | 1/2016 | Hargreaves | G01J 3/453 |
| | | | 356/301 |
| 2017/0026588 A1* | 1/2017 | Kester | G01J 5/0014 |
| 2017/0059408 A1* | 3/2017 | Korner | G01B 11/2536 |
| 2017/0122923 A1* | 5/2017 | Chok | G01N 21/31 |
| 2017/0281007 A1 | 10/2017 | Pyun et al. | |
| 2018/0053038 A1* | 2/2018 | Robinson | G06T 7/70 |
| 2018/0120155 A1* | 5/2018 | Rosen | G01J 3/0286 |
| 2019/0065696 A1* | 2/2019 | Basener | G01N 21/31 |
| 2019/0101444 A1 | 4/2019 | Yoon et al. | |
| 2019/0154503 A1 | 5/2019 | Yoon et al. | |

OTHER PUBLICATIONS

Cheng-Chun Chang et al. "On the estimation of target spectrum for filter-array based spectrometers", Optics Express, vol. 16, No. 2, Jan. 21, 2008 (pp. 1056-1061).

* cited by examiner

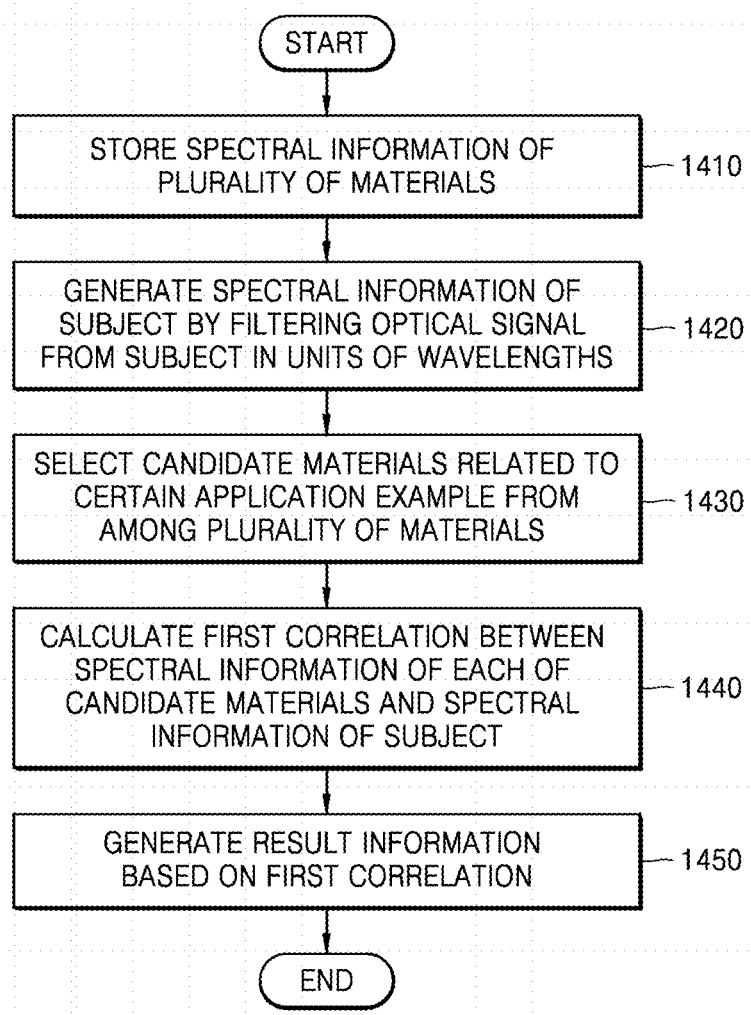

METHOD AND APPARATUS FOR ANALYZING SPECTRAL INFORMATION

CROSS-REFERENCE TO RELATED APPLICATION

This application claims priority from Korean Patent Application No. 10-2018-0120614, filed on Oct. 10, 2018, in the Korean Intellectual Property Office, the disclosure of which is herein incorporated by reference in its entirety.

BACKGROUND

1. Field

Methods and apparatuses consistent with exemplary embodiments relate to methods and apparatuses for analyzing spectral information.

2. Description of the Related Art

A chemical or physiological state of a subject may be identified by analyzing spectral information of an optical signal generated from the subject. For example, a blood cholesterol concentration or a blood sugar level may be measured by analyzing spectral information of blood, and whether food spoils may be determined by analyzing spectral information of the food.

Research has been conducted to reduce the size of a spectroscopic apparatus for analyzing spectral information of a subject. In particular, an image sensor type spectroscopic apparatus that is provided on a single chip and thus may be mounted into a portable terminal or the like has been introduced.

As the size of the spectroscopic apparatus is reduced, the performance of the spectroscopic, e.g., a resolution for distinguishing different spectral signals from each other, may deteriorate. Accordingly, there is a need for a technique for maintaining high performance, e.g., a high resolution, of a spectroscopic apparatus even when the size of the spectroscopic apparatus is small.

SUMMARY

Exemplary embodiments provide methods and apparatuses for analyzing spectral information. In particular, exemplary embodiments provide methods and apparatuses for analyzing spectral information with higher performance and a smaller size of the apparatuses.

Additional aspects will be set forth in part in the description which follows and, in part, will be apparent from the description, or may be learned by practice of the exemplary embodiments.

According to an aspect of an exemplary embodiment, there is provided an apparatus for analyzing spectral information including a database configured to store spectral information of a plurality of materials analyzed by the apparatus, a spectroscopic unit configured to generate spectral information of a subject by filtering an optical received from the subject in units of wavelengths, and a controller configured to obtain correlations between spectral information of each of candidate materials from among the plurality of materials and the spectral information of the subject, and generate result information based on the correlations.

The controller may be further configured to select at least one final material of which a correlation with the spectral information of the subject among the correlations is greater than a reference value from among the candidate materials, and generate the result information regarding the at least one final material.

The result information may include information indicating whether the at least one final material is detected from the subject, and a concentration of the at least one final material in the subject.

The controller may be further configured to adjust the reference value and select the at least one final material based on the adjusted reference value.

The spectroscopic unit may include at least one spectral filter configured to filter the optical signal in the units of wavelengths, the at least one spectral filter each including a plurality of spectral channels which are set to pass different wavelengths of the optical signal; and an image sensor configured to generate the spectral information of the subject, based on at least one filter signal generated by the at least one spectral filter. The at least one filter signal may represent intensities of wavelength band signals passing through the plurality of spectral channels.

The controller may be further configured to obtain an average filter signal for the at least one filter signal, second correlations between each of the at least one filter signal and the average filter signal, and generate the spectral information of the subject, based on the second correlations between each of the at least one filter signal and the average filter signal.

The controller may be further configured to select at least one filter signal of which a second correlation with the average filter signal among the second correlations is greater than a reference value from among the at least one filter signal, and generate the spectral information of the subject based on an average signal for the at least one filter signal having the second correlation greater than the reference value.

The apparatus may further include a light source configured to emit light onto the subject. The optical signal may be generated from the light emitted onto the subject.

The controller may be further configured to select the candidate materials based on information regarding a chemical and/or physiological state of the subject.

The spectroscopic unit may be provided as a system-on-chip.

According to an aspect of another exemplary embodiment, there is provided a method of analyzing spectral information including storing spectral information of a plurality of materials, generating spectral information of a subject by filtering an optical received from the subject in units of wavelengths, obtaining correlations between spectral information of each of candidate materials from among the plurality of materials and the spectral information of the subject; and generating result information based on the correlations.

According to an aspect of still another exemplary embodiment, there is provided a non-transitory computer-readable recording medium having recorded thereon a program, which, when executed by at least one processor, causes the at least one processor to perform: storing spectral information of a plurality of materials; generating spectral information of a subject by filtering an optical signal received from the subject in units of wavelengths; obtaining correlations between spectral information of each of candidate materials from among the plurality of materials and the spectral information of the subject; and generating result information based on the correlations.

BRIEF DESCRIPTION OF THE DRAWINGS

The above and/or other aspects will become apparent and more readily appreciated from the following description of the exemplary embodiments, taken in conjunction with the accompanying drawings in which:

FIG. 14 is a flowchart of a method of analyzing spectral information, according to an exemplary embodiment.

DETAILED DESCRIPTION

Figure 1:
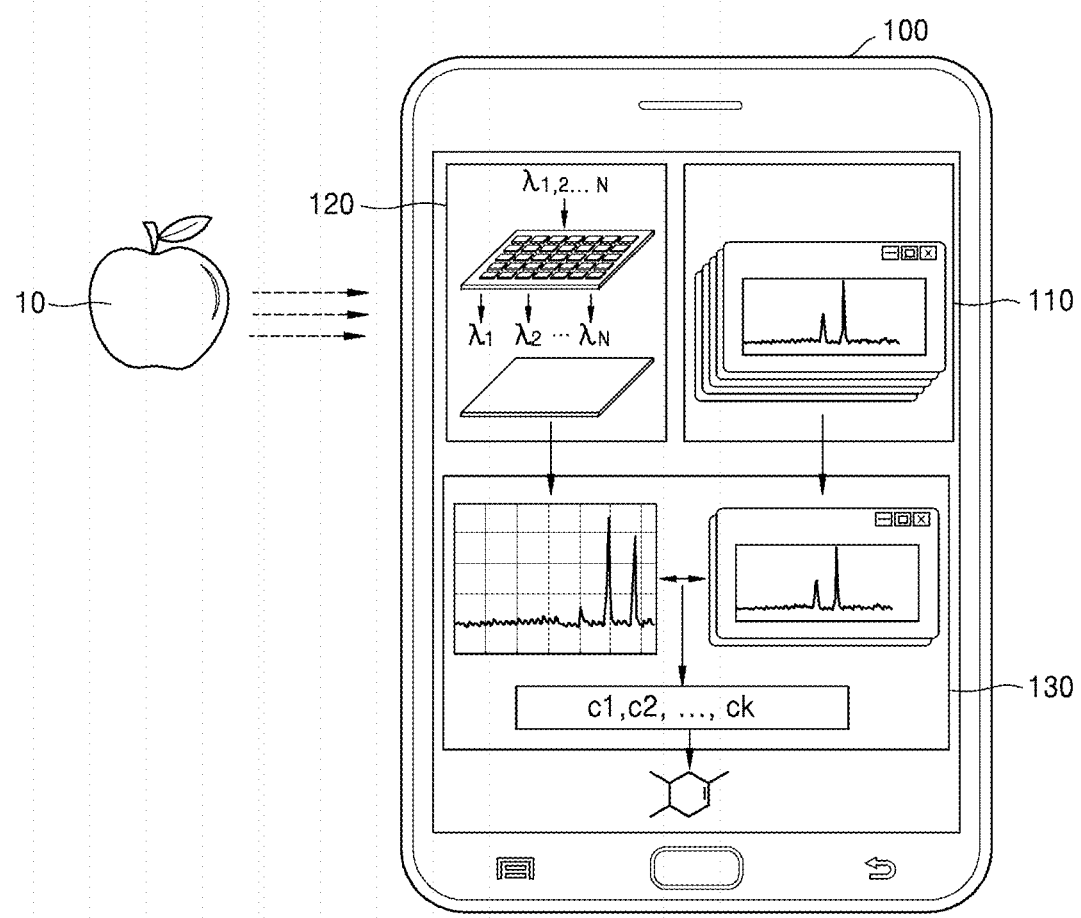
FIG. 1 is a diagram illustrating a process of analyzing spectral information according to an exemplary embodiment.

Reference will now be made in detail to embodiments, examples of which are illustrated in the accompanying drawings, wherein like reference numerals refer to like elements throughout. The exemplary embodiments may have different forms and should not be construed as being limited to the descriptions set forth herein. Accordingly, some of the exemplary embodiments are merely described below, by referring to the figures, to explain aspects of the disclosure. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

In exemplary embodiments set forth herein, general terms that have been widely used nowadays are selected, if possible, in consideration of functions of the exemplary embodiments, but non-general terms may be selected according to the intentions of technicians in the this art, precedents, or new technologies, etc. Some terms may be arbitrarily chosen by the applicant. In this case, the meanings of these terms will be explained in corresponding parts of the disclosure in detail. Thus, the terms used herein should be defined not based on the names thereof but based on the meanings thereof and the whole context of the exemplary embodiments.

In the exemplary embodiments, it will be understood that when an element is referred to as being "connected to" another element, the element may be directly connected to another element or may be electrically connected to another element while having intervening elements therebetween. It will be understood that when an element is referred to "including" another element, the element may further other elements unless mentioned otherwise.

The terms "comprises" and/or "comprising" used herein should not be construed as necessarily including all various elements or operations described herein and should be understood that some of the elements or operations may be omitted or additional elements or operations may be further provided.

It will be understood that, although the terms first, second, third, etc., may be used herein to describe various elements, these elements should not be limited by these terms. These terms are only used to distinguish one element from another element. In addition, the terms, such as 'part' or 'unit', etc., should be understood as a unit that performs at least one function or operation and that may be embodied as hardware, software, or a combination thereof.

The following description of the exemplary embodiments should not be construed as limiting the scope of the disclosure, and modifications to the embodiments that would be easily derived by those of ordinary skill in the art should be construed as being within the scope of the disclosure. Hereinafter, for only illustrative purposes, exemplary embodiments will be described in detail with reference to the accompanying drawings.

FIG. 1 is a diagram illustrating a process of analyzing spectral information according to an exemplary embodiment.

FIG. 1 illustrates a process of analyzing spectral information of a subject 10 by an apparatus 100 for analyzing spectral information. However, the process illustrated in FIG. 1 is merely an example and thus a process of analyzing spectral information according to the disclosure is not limited thereto.

The spectral information may be information regarding an optical signal emitted from a material of the subject 10. The optical signal may be an electromagnetic wave radiated from the material of the subject 10. Alternatively, the optical signal may be a signal emitted as natural light or light provided by the apparatus 100 is reflected, absorbed or scattered according to unique characteristics of the material of the subject 10. Information about the material of the subject 10 may be obtained by analyzing spectral information of the optical signal.

The subject 10 may be a target to be analyzed by using an apparatus and/or a method of analyzing spectral information according to an exemplary embodiment. For example, the optical signal may be generated from the material of the subject 10, and the subject 10 may be a target, the chemical or physiological state of which is to be analyzed, e.g., food, clothing, blood, or tap water.

In the process of analyzing spectral information according to the disclosure, certain application examples may be considered, in addition to the subject 10. For example, when the subject 10 is food, an application example may be to provide information regarding the freshness of the food, whether the food contains a certain nutrient, whether the food spoils, or the like. As another example, when the subject 10 is blood, an application example may be to provide information regarding a blood cholesterol concentration, a blood glucose level, or the like.

An application example may be to provide information about the chemical or physiological state of the subject 10 based on the spectral information of the subject 10. A criteria for determining the chemical or physiological state of the subject 10 may vary according to an application example. Application examples may be set in advance and provided during the analyzing of spectral information.

An application example may be selected by a user of the apparatus 100 for analyzing spectral information. For example, before the apparatus 100 receives an optical signal generated from the material of the subject 10, the user may select one of a plurality of application examples, which are set in advance and stored in the apparatus 100, via a user interface or the like.

The apparatus 100 may store spectral information of a plurality of materials. In detail, a database 110 included in the apparatus 100 may store spectral information of a plurality of materials measured in advance. The plurality of materials may be targets to be detected in relation to application examples, including a certain nutrient, a toxic substance due to food spoilage, glucose in the blood, etc.

The database 110 of the apparatus 100 may store information regarding a plurality of application examples. Thus, the user of the apparatus 100 may select one of the plurality of application examples.

As an application example is determined, the apparatus 100 may select at least one candidate material. In detail, a controller 130 included in the apparatus 100 may select candidate materials related to the determined application example from among the plurality of materials stored in the database 110.

The apparatus 100 may receive an optical signal from the subject 10 and generate spectral information of the subject 10. In detail, a spectroscopic unit (e.g., a spectroscopic) 120 included in the apparatus 100 may generate the spectral information of the subject 10 by filtering an optical signal received from the subject 10 in units of wavelengths.

The apparatus 100 may calculate a correlation between spectral information of each of the candidate materials and the spectral information of the subject 10. In detail, as the application example is selected, the controller 130 of the apparatus 100 may calculate the correlation between the spectral information of each of the candidate materials selected from among the plurality of materials stored in the database 110 and the spectral information of the subject 10 generated by the spectroscopic unit 120.

The apparatus 100 may generate result information, based on the calculated correlation. The result information may be information regarding at least one final material selected from among the candidate materials, which are selected from among the plurality of materials stored in the database 110, according to a certain criterion as the application example is selected. For example, when the subject 10 is an apple, fructose may be selected from the candidate materials, and the result information may be information about fructose in the apple.

A related art spectroscopic apparatus may generate a reconstructed spectrum by applying a spectral reconstruction algorithm to the spectral information of the subject 10 and provide result information by using the generated reconstructed spectrum. Therefore, in the related art, an excessive amount of calculations may be required during the process of generating the reconstructed spectrum by applying the spectral reconstruction algorithm to the spectral information of the subject 10, and an accurate spectral reconstruction algorithm may be required.

Unlike the related art spectroscopic apparatus, the apparatus 100 for analyzing spectral information according to the disclosure may provide the result information, based on the correlation between the spectral information of the subject 10 and the spectral information of each of the plurality of materials stored in the database 110.

The apparatus 100 for analyzing spectral information according to the disclosure is capable of providing result information by a correlation analysis method using the database 110 without generating a reconstructed spectrum, thereby reducing the amount of calculations required to provide the result information.

Figure 2:
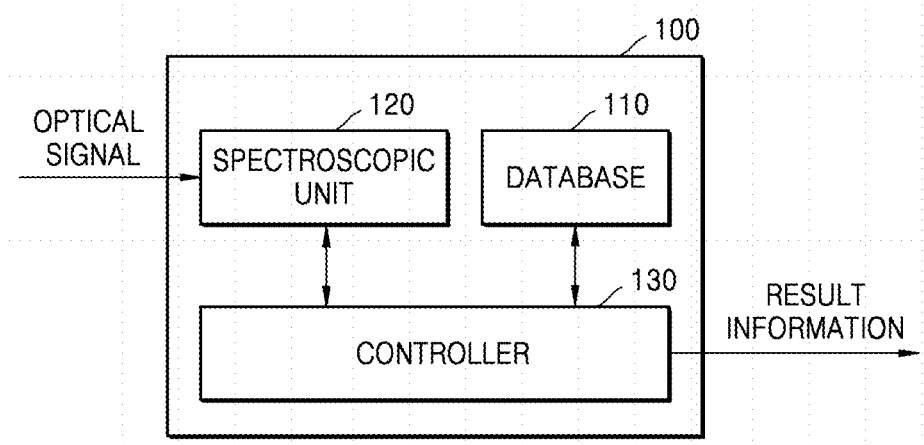
FIG. 2 is a block diagram illustrating a structure of an apparatus for analyzing spectral information, according to an exemplary embodiment.

FIG. 2 is a block diagram illustrating a structure of an apparatus for analyzing spectral information, according to an exemplary embodiment.

Referring to FIG. 2, an apparatus 100 for analyzing spectral information may include a database 110, a spectroscopic unit 120, and a controller 130. However, it will be apparent to those skilled in the art that exemplary embodiments are not limited thereto and the apparatus 100 may further include other general components, as well as the components illustrated in FIG. 2.

The database 110 may store spectral information of a plurality of materials. The database 110 may store data processed by or to be processed by the controller 130. In particular, the database 110 may store spectral information of a plurality of materials which are targets to be detected in relation to application examples.

The database 110 may be embodied as, but is not limited to, a dynamic random access memory (DRAM), a static random access memory (SRAM), a read-only memory (ROM), an electrically erasable programmable read-only memory (EEPROM), a compact disc (CD)-ROM, a Blu-ray disc, a hard disk drive (HDD), a solid-state drive (SSD), or a flash memory.

The spectroscopic unit 120 may receive an optical signal from the subject 10 and generate spectral information of the subject 10 by filtering the received optical signal in units of wavelengths. The spectral information of the subject 10 may be a result of filtering an optical signal emitted from the subject 10 by the spectroscopic unit 120. The spectroscopic unit 120 may generate the spectral information of the subject 10, based on intensities of wavelength band signals of the optical signal.

The spectroscopic unit 120 may generate the spectral information of the subject 10 by an image sensor-based spectroscopic method. For example, the spectroscopic unit 120 may include at least one spectral filter of a filter array and may receive the optical signal from the subject 10 through the at least one spectral filter. The spectroscopic unit 120 may generate the spectral information of the subject 10 by receiving at least one filter signal passing through the at least one spectral filter via the image sensor. However, exemplary embodiments are not limited thereto, and the spectroscopic unit 120 may generate the spectral information of the subject 10 by a quantum dot (QD) spectroscopic method.

The spectroscopic unit 120 may analyze the spectral information of the subject 10 by the image sensor-based spectroscopic method and thus the size of the spectroscopic unit 120 may be reduced. The image sensor-based spectroscopic method or the QD type spectroscopic method is a planar spectroscopic method, in which a hardware configuration for performing spectroscopy may be implemented on an integrated circuit substrate.

Thus, the spectroscopic unit 120 that generates the spectral information of the subject 10 by the image sensor-based spectroscopic method may be manufactured in a smaller size than that in a related art grating-based dispersive spectroscopic method. In particular, when the size of the spectroscopic unit 120 is substantially reduced, the spectroscopic unit 120 may be implemented as a system-on-chip.

When the spectroscopic unit 120 may be implemented as a system-on-chip, the apparatus 100 for analyzing spectral information according to the disclosure may be included in a portable terminal device such as a smart phone or a tablet PC. When the apparatus 100 may be included in the portable terminal device, the portability and usability of the apparatus 100 may be greatly increased.

The spectroscopic unit 120 according to an exemplary embodiment will be described in detail with reference to FIG. 3 below.

Figure 3:
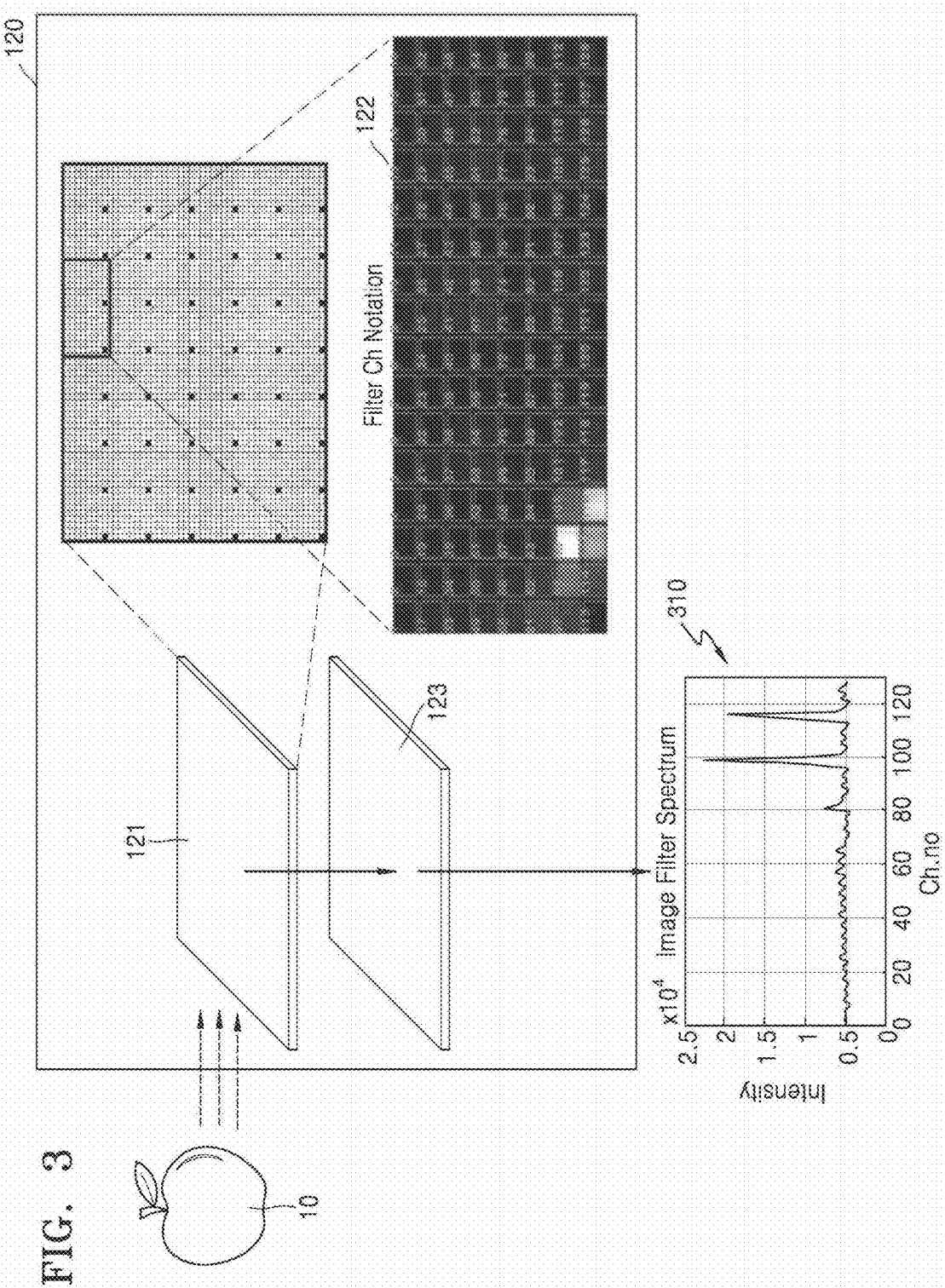
FIG. 3 is a diagram illustrating a spectroscopic unit according to an exemplary embodiment.

FIG. 3 is a diagram illustrating a spectroscopic unit according to an exemplary embodiment.

Referring to FIG. 3, a spectroscopic unit 120 may include at least one spectral filter 121 and an image sensor 123. However, other general-purposes components may be further included in the spectroscopic unit 120, as well as the components illustrated in FIG. 3.

The at least one spectral filter 121 may include a plurality of spectral filers. However, exemplary embodiments are not limited thereto and the at least one spectral filter 121 may include one spectral filter. The following description of a case in which the at least one spectral filter 121 includes a plurality of spectral filters may apply to a case in which the at least one spectral filter 121 includes one spectral filter.

Each of the plurality of spectral filters may include a plurality of spectral channels 122. The plurality of spectral filters may form a filter array. For example, the plurality of spectral filters may include 24 spectral filters, and the 24 spectral filters may form a 4×6 filter array. Each of the 24 spectral filters may include 128 spectral channels. Thus, the plurality of spectral filters may include a total of 3072 spectral channels. However, exemplary embodiments are not limited thereto, and the number of spectral filters of the filter array may be changed.

Each of the plurality of spectral channels 122 may be set to pass different wavelength bands of an optical signal received from the subject 10. When the plurality of spectral channels 122 are set to pass different wavelength bands of the optical signal, the plurality of spectral channels 122 may filter the optical signal in units of wavelengths.

The optical signal may include a plurality of signal components, and the plurality of signal components may have different wavelength bands. When the optical signal is filtered by the plurality of spectral channels 122 in units of wavelengths, the optical signal may be spectrally divided into a plurality of signal components having different wavelength bands. When the optical signal is filtered in units of wavelengths, the intensities of wavelength band signals passing through the plurality of spectral channels 122 may be obtained.

The image sensor 123 may generate spectral information of the subject 10, based on at least one filter signal generated by the plurality of spectral filers. The at least one filter signal may represent the intensities of wavelength band signals passing through the plurality of spectral channels 122

The at least one filter signal may include a plurality of filter signals. However, exemplary embodiments are not limited thereto and the at least one filter signal may be one filter signal. A description of a case in which the at least one filter signal includes the plurality of filter signals may also apply to a case in which the at least one filter signal is one filter signal.

Each of the plurality of spectral filers may include a plurality of spectral channels 122, and an optical signal may be filtered in units of wavelengths by the plurality of spectral channels 122, thereby generating a plurality of filter signals by the plurality of spectral filters. For example, 24 filter signals may be generated by 24 spectral filters.

The plurality of filter signals generated by the plurality of spectral filters may represent the intensities of wavelength band signals passing through the plurality of spectral channels 122. For example, the plurality of spectral channels 122 may include 128 spectral channels corresponding to 128 wavelength bands, and the filter signals may include the intensities of 128 signals as the intensities of signals corresponding to wavelength bands.

The image sensor 123 may generate spectral information of the subject 10, based on the plurality of filter signals. For example, the image sensor 123 may receive a plurality of filter signals from the plurality of spectral filters and may generate the spectral information of the subject 10 by calculating an averaged filter signal for the plurality of filter signals In a graph 310 of FIG. 3 illustrating spectral information of the subject 10, the horizontal axis represents consecutive numbers corresponding to the plurality of spectral channels 122, and the vertical axis represents signal intensities corresponding to the plurality of spectral channels 122. For example, when the plurality of spectral channels 122 include 128 spectral channels corresponding to 128 wavelength bands, the spectral information of the subject 10 may include the signal intensities corresponding to the 128 wavelength bands. Values on the vertical axis may be understood to indicate signal intensities relatively represented by 65536 values ranging from 0 to 65535 corresponding to 16 bits.

The plurality of spectral channels 122 included in each of the plurality of spectral filters will be described in detail with reference to FIG. 4 below.

Figure 4:
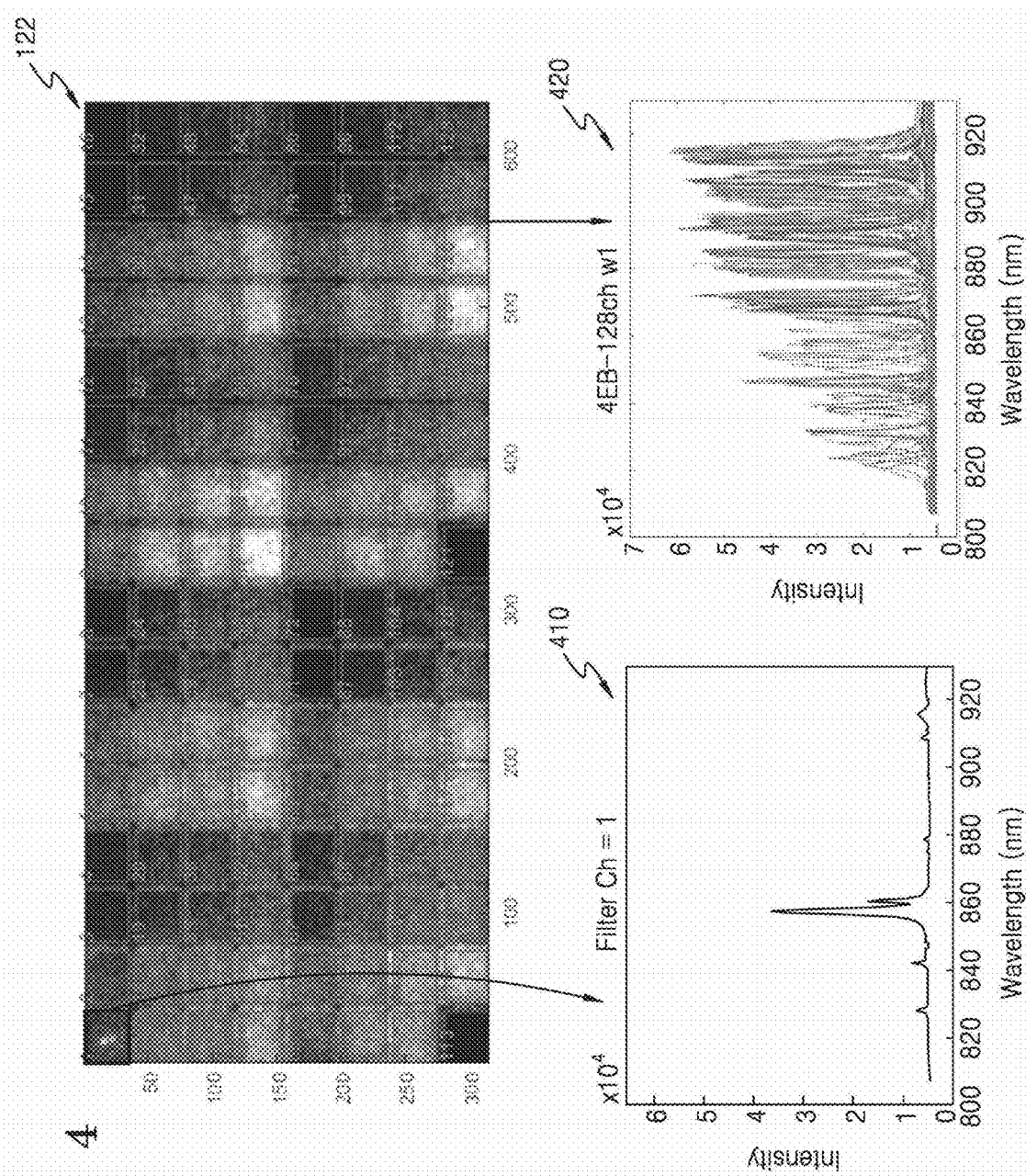
FIG. 4 is a diagram illustrating a plurality of spectral channels according to an exemplary embodiment.

FIG. 4 is a diagram illustrating a plurality of spectral channels according to an exemplary embodiment.

FIG. 4 illustrates a plurality of spectral channels 122 and transmittances of the plurality of spectral channels 122 in units of wavelengths. For example, the plurality of spectral channels 122 may include 128 spectral channels and consecutive numbers of 1 to 128 may be assigned to the 128 spectral channels.

A graph 410 may show transmittances of the spectral channel 1 in units of wavelengths. A graph 420 may show transmittances of all the 128 spectral channels in units of wavelengths.

Referring to the graph 410, the spectral channel 1 may pass a component of an optical signal corresponding to a wavelength band of about 860 nm and may not pass the other components of the optical signal corresponding to the other wavelengths. Similarly, the 128 spectral channels may be set to pass different wavelength bands of the optical signal. Thus, the graph 420 shows the transmittances of all the 128 spectral channels in units of wavelengths.

The plurality of spectral channels 122 may be embodied as band-pass filters configured to pass different wavelength bands of the optical signal. Thus, the plurality of spectral channels 122 may be embodied as a plurality of band-pass filters configured to pass different wavelength bands of the optical signal.

Referring to the graph 420, the transmittances of the plurality of spectral channels 122 may not be uniform. In addition, the wavelength bands set for the plurality of spectral channels 122 may partially overlap each other. Originally, the plurality of spectral channels 122 are designed to have a uniform transmittance and to have wavelength bands that do not overlap with each other but the transmittance and the wavelength bands may become non-uniform through a manufacturing process.

Such non-uniform characteristics of the plurality of spectral channels 122 may lead to errors in the spectral information of the subject 10. Since in the related art spectroscopic method, a reconstructed spectrum is generated by applying the spectral reconstruction algorithm to the spectral information of the subject 10, when the spectral information of the subject 10 has the errors, the reconstructed spectrum may also have errors and the number of errors in the reconstructed spectrum may increase during the application of the spectral reconstruction algorithm.

In contrast, in the apparatus 100 for analyzing spectral information according to the disclosure, result information may be generated by the correlation analysis method using the database 110 without providing a reconstructed spectrum through the spectral reconstruction algorithm. When the spectral information of the plurality of materials stored in the database 110 and the spectral information of the subject 10 are obtained by the same apparatus 100, a degree of errors in the spectral information of the plurality of materials and a degree of errors in the spectral information of the subject 10 may be substantially the same. Since a correlation between a plurality of pieces of spectral information having substantially the same degree of errors is calculated, the substantially same degree of errors contained in the spectral information may be compensated for during the calculation of the correlation. Accordingly, the apparatus 100 is capable of significantly reducing errors caused by non-uniform characteristics due to the manufacturing process, as compared with the related art spectroscopic method.

Referring back to FIG. 2, the apparatus 100 may include the controller 130. The controller 130 may be embodied as either an array of a plurality of logic gates or a combination of a general-purpose microprocessor and a memory storing a program executable by the general-purpose microprocessor. Alternatively, the controller 130 may be embodied as a plurality of processing elements.

The controller 130 may select candidate materials related to a certain application example from among a plurality of materials, calculate a first correlation between spectral information of each of the candidate materials and the spectral information of the subject 10, and generate result information, based on the first correlation. Operations performed by the controller 130 will described in detail with reference to FIGS. 5 to 7 below.

Figure 5:
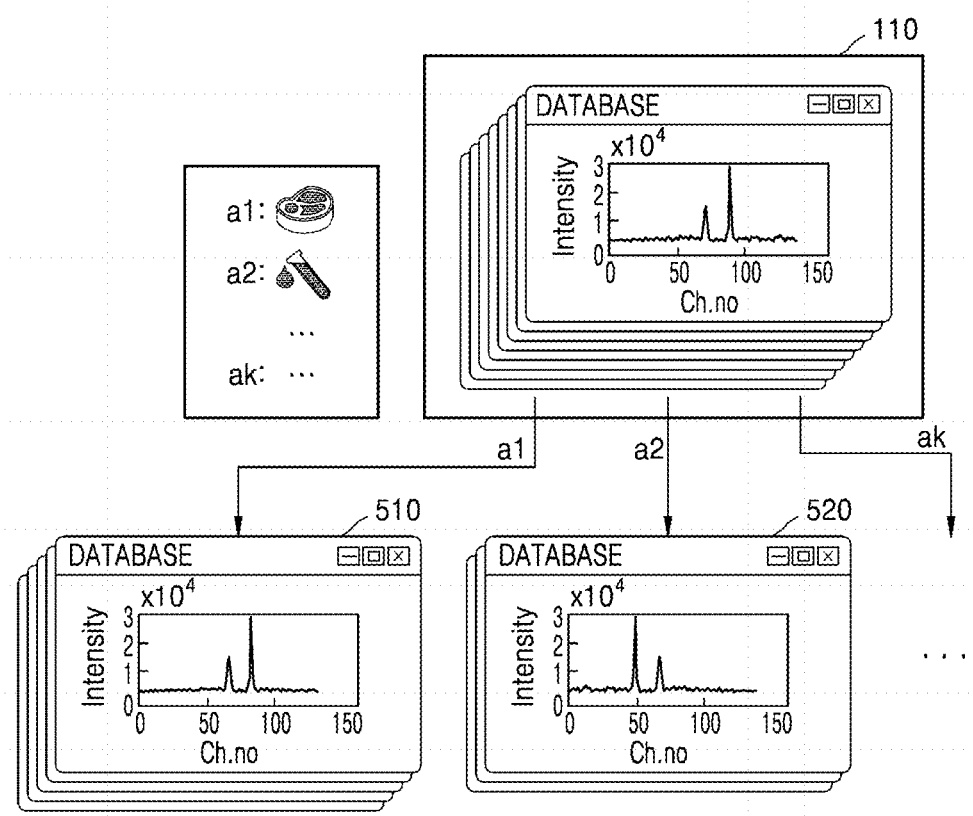
FIG. 5 is a diagram illustrating a process of selecting spectral information of candidate materials related to a certain application example from a database, according to an exemplary embodiment.

FIG. 5 is a diagram illustrating a process of selecting spectral information of candidate materials related to a certain application example from a database, according to an exemplary embodiment.

Referring to FIG. 5, the controller 130 may select candidate materials related to a certain application example from among a plurality of materials. In detail, the controller 130 may select candidate materials related to at least one application example among a plurality of application examples a1, a2, . . . , ak from among a plurality of materials related to spectral information stored in the database 110.

The plurality of application examples a1, a2, . . . , ak may be set in advance and be provided. At least one of the plurality of application examples a1, a2, . . . , ak may be selected by a user of the apparatus 100. The plurality of application examples a1, a2, . . . , ak may be stored in the apparatus 100. For example, the plurality of application examples a1, a2, . . . , ak may be stored in the database 110 and a list thereof may be updated.

The candidate materials may be materials related to at least one application example, which is selected from among the plurality of application examples a1, a2, . . . , ak, among the plurality of materials related to the spectral information stored in the database 110. For example, when an application example is to determine whether food spoils, the controller 130 may select, as candidate materials, oxygen, moisture, putrefactive bacteria, nitrogen compounds, sulfur compounds, yeast, etc. from among the plurality of materials stored in the database 110.

The candidate materials selected from the database 110 by the controller 130 may vary depending on an application example selected. For example, when the application example a1 is selected, the controller 130 may select candidate materials related to the application example a1 from among the plurality of materials stored in database 110 and thus spectral information 510 regarding the candidate materials related to the application example a1 may be selected. Alternatively, when the application example a2 is selected, spectral information 520 regarding candidate materials related to the application example a2 may be selected.

Figure 6:
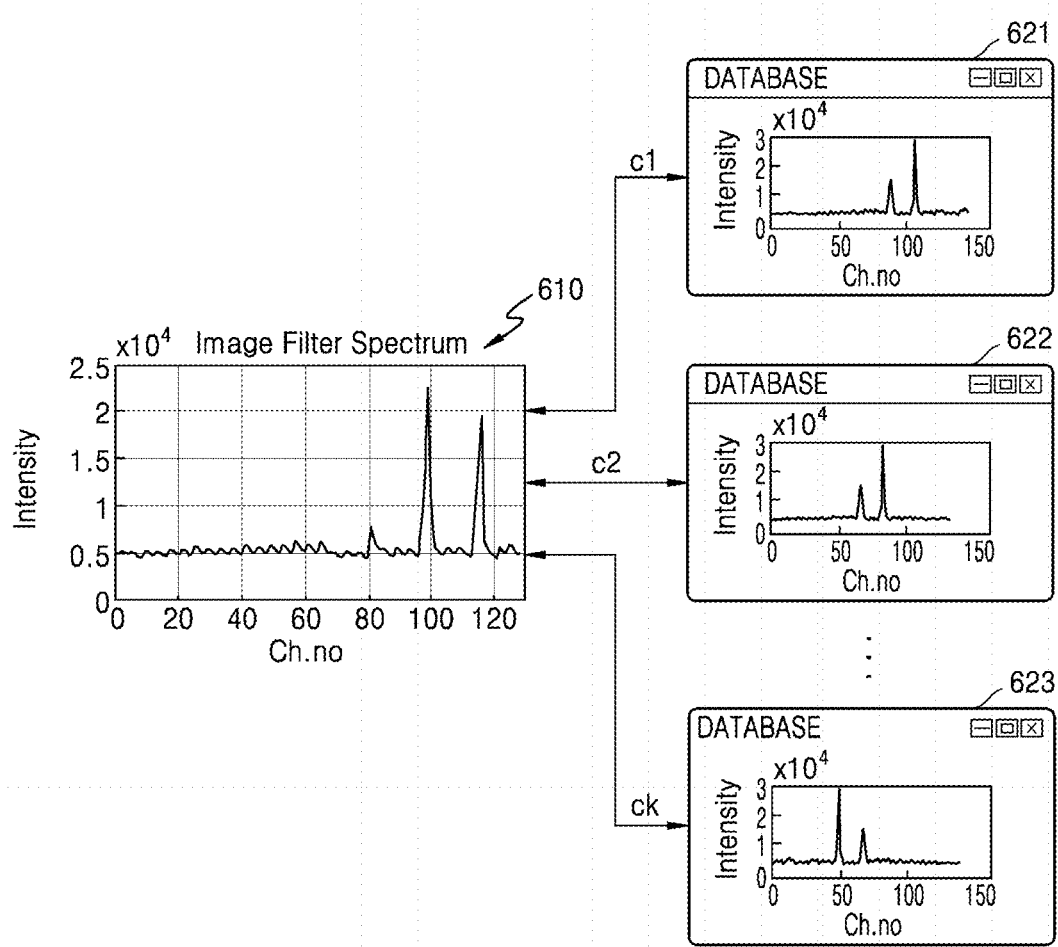
FIG. 6 is a diagram illustrating a process of calculating a first correlation between spectral information of each of candidate materials and spectral information of a subject, according to an exemplary embodiment.

FIG. 6 is a diagram illustrating a process of calculating a first correlation between spectral information of each of candidate materials and spectral information of a subject, according to an exemplary embodiment.

Referring to FIG. 6, the controller 130 may calculate first correlations c1, c2, . . . , ck between spectral information 610 regarding the subject 10 and spectral information 621, 622, . . . , 623 regarding respective candidate materials. Spectral information of a plurality of materials, including the spectral information 621, 622, . . . , 623 regarding the respective candidate materials, may be stored in the database 110.

In the disclosure, a correlation, including first and second correlations, may be an indicator indicating a degree of correlation or similarity between two pieces of spectral information. The correlation may be a value ranging from 0 to 1. The closer the correlation is to 1, the more the two pieces of spectral information may be related and similar to each other.

The correlation may be calculated based on the intensities of wavelength band signals passing through the plurality of spectral channels 122. For example, when the plurality of spectral channels 122 include 128 spectral channels, spectral information 610 regarding the subject 10 and the spectral information 621, 622, . . . , and 623 regarding the respective candidate materials may include 128 signal intensities.

For example, the controller 130 may calculate a first correlation c1 by comparing the intensities of signals for spectral channels corresponding to the spectral information 610 regarding the subject 10 and the spectral information 621 regarding one of the candidate materials 128 times. Similarly, the controller 130 may calculate first correlations c2, . . . , ck with respect to the spectral information 622, . . . , 623 regarding the other candidate materials. As one example, a correlation may be embodied as a Jacquard index.

Figure 7:
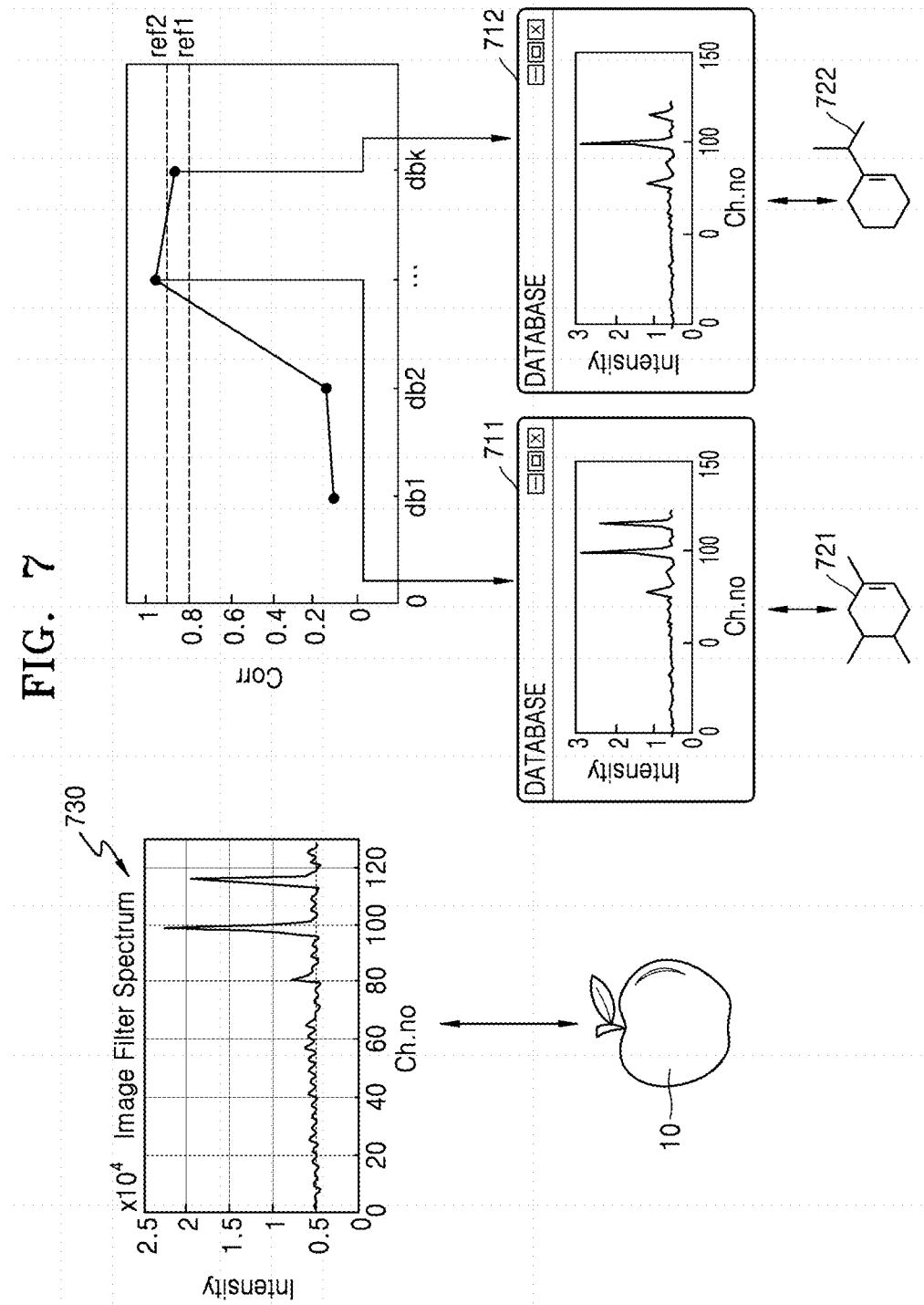
FIG. 7 is a diagram illustrating a process of generating result information, based on the first correlation, according to an exemplary embodiment.

FIG. 7 is a diagram illustrating a process of generating result information, based on a first correlation, according to an exemplary embodiment.

Referring to FIG. 7, the controller 130 may generate result information, based on a first correlation. In detail, the controller 130 may generate result information, based on a first correlation between spectral information of each of candidate materials and spectral information of a subject 10.

The controller 130 may select at least one final material having a first correlation greater than a reference value from among the candidate materials. The at least one final material may include a plurality of final materials. However, exemplary embodiments are not limited thereto, and the at least one final material may be one final material. A description of a case in which the at least one final material includes a plurality of final materials may also apply to a case in which the at least one final material is one final material.

For example, the controller 130 may select first spectral information 711 having a correlation cx greater than a reference value ref1 and second spectral information 712 having a correlation cy greater than the reference value ref1 and select a first material 721 corresponding to the first spectral information 711 and a second material 722 corresponding to the second spectral information 712 as final materials.

When the first material 721 and the second material 722 are selected as final materials, the controller 130 may generate information related to the first material 721 and the second material 722 as result information which is information regarding the subject 10.

The result information may include at least one of information indicating whether the final materials are detected from the subject 10 and concentrations of the final materials in the subject 10. For example, when the first material 721 and the second material 722 are selected as final materials, the result information may include at least one of information indicating whether the first material 721 and the second material 722 are detected from the subject 10 and concentrations of the first material 721 and the second material 722 in the subject 10.

The result information may be obtained based on peak characteristics of the spectral information. The peak characteristics of the spectral information may include the intensities of the peaks, channels of the peaks, etc. For example, when the first material 721 is selected as a final material, the controller 130 may generate result information by comparing peak characteristics of the first spectral information 711 regarding the first material 721 and peak characteristics of spectral information 730 regarding the subject 10 with each other. In detail, whether the first material 721 is detected from the subject 10 may be determined, based on whether channels of peaks are the same, and the concentration or density of the first material 721 in the subject 10 may be determined, based on the intensities of the peaks.

As the result information includes at least one of the information indicating whether the final materials are detected from the subject 10 and the concentrations of the final materials in the subject 10, purposes of various application examples requesting to determine whether a certain material is in the subject 10 or the concentration of the material of the subject 10 is measured may be achieved.

The controller 130 may adjust the reference value to improve the accuracy of the result information and select the at least one final material based on the adjusted reference value. For example, the controller 130 may adjust the reference value, based on a target number of final materials. When the reference value ref1 is set as illustrated in FIG. 7, the final materials may include the first material 721 and the second material 722. The controller 130 may adjust the reference value ref1 to a reference value ref2. When the reference value ref1 is adjusted to the reference value ref2, the first material 721 may be a final material. As the reference value ref1 is adjusted to the reference value ref2, only the first material 721 is selected and thus the accuracy of analyzing the spectral information of the subject 10 may be improved.

However, exemplary embodiments are not limited to the example in which the reference value ref1 is increased to the reference value ref2, and the controller 130 may change a method of adjusting a reference value according to a purpose of analyzing the spectral information of the subject 10. For example, in the case of an application example requesting a large number of final materials, the controller 130 may reduce the reference value.

Referring back to FIG. 2, the apparatus 100 may further include a light source (not shown), as well as the database 110, the spectroscopic unit 120, and the controller 130.

The light source may emit light onto the subject 10. An optical signal may be generated, as the subject 10 absorbs some wavelengths of the light emitted from the light source and reflects the other wavelengths. Accordingly, an optical signal received from the subject 10 by the spectroscopic unit 120 may be generated from the light emitted onto the subject 10.

The light emitted from the light source may be light of a plurality of wavelength bands. Alternatively, the light emitted from the light source may be light of wavelength bands falling within a range determined according to a particular purpose. For example, the light emitted from the light source may be near-infrared rays of wavelength bands of about 750 nm to about 3,000 nm The apparatus 100 further includes the light source and thus may analyze spectral information of the subject 10 even in the absence of natural light.

Figure 8:
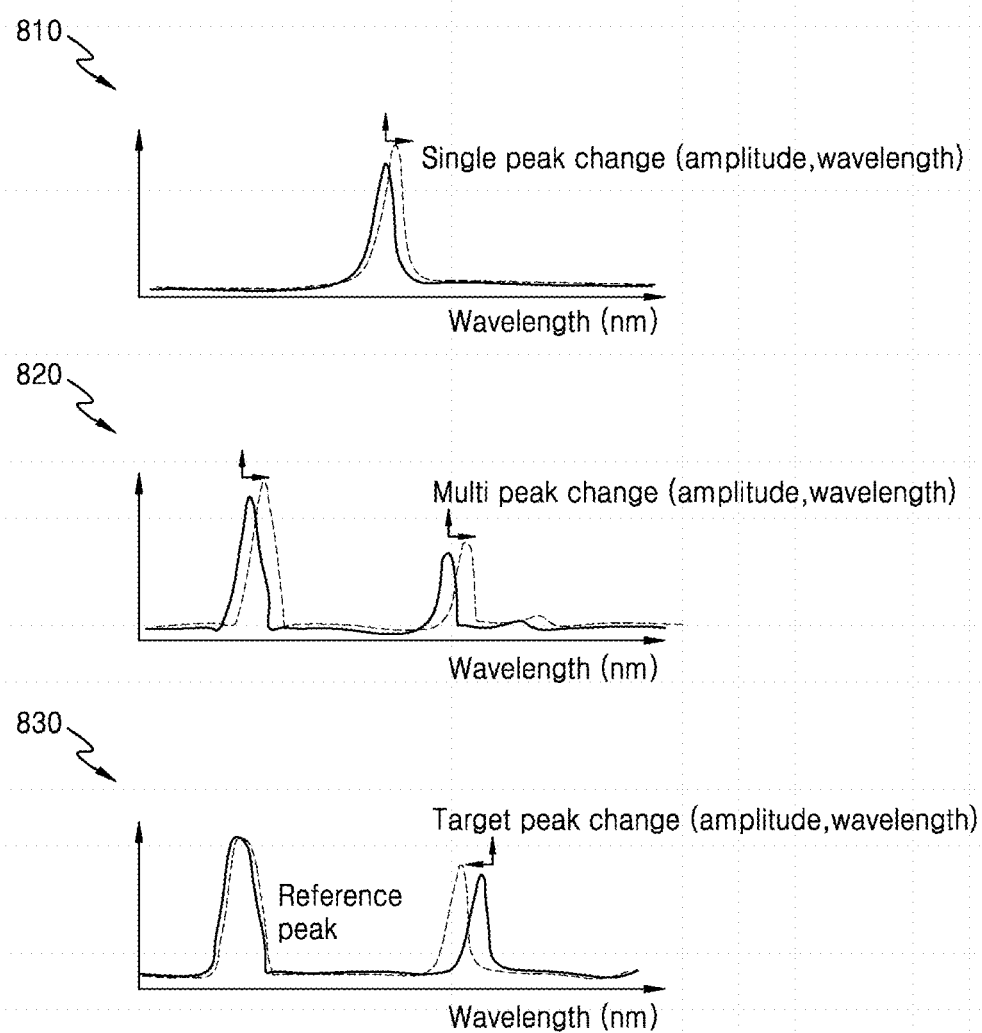
FIG. 8 is a diagram illustrating a process of analyzing a reconstructed spectrum generated from result information regarding at least one final material, according to an exemplary embodiment.

FIG. 8 is a diagram illustrating a process of analyzing a reconstructed spectrum generated from result information regarding at least one final material, according to an exemplary embodiment.

FIG. 8 illustrates three methods of analyzing a reconstructed spectrum. The apparatus 100 for analyzing spectral information according to the disclosure may generate a reconstructed spectrum by applying a reconstruction algorithm to result information regarding at least one final material. The reconstruction algorithm applied by the apparatus 100 may be a simple reconstruction method of generating a reconstructed spectrum from result information according to a wavelength band corresponding to each of the plurality of spectral channels 122.

The database 110 included in the apparatus 100 may store spectral data measured accurately with respect to a plurality of materials, as well as spectral information of the plurality of materials.

The apparatus 100 may analyze the reconstructed spectrum by comparing the reconstructed spectrum reconstructed from the result information and the spectral data stored in the database 110 with each other.

In order to compare the reconstructed spectrum and the spectral data with each other, a change in a wavelength may be analyzed as shown in a graph 810, changes in a plurality of wavelengths may be analyzed as shown in a graph 820, or a change in a wavelength may be analyzed with respect to a certain wavelength as a reference wavelength as shown in a graph 830.

A change in the intensity of a peak may be understood to mean that the concentration or density of a material corresponding to the peak is changed. A change in a wavelength band at which a peak occurs may be understood to mean that a material corresponding to the peak is reacted with or bonded to another material The apparatus 100 may provide result information, based on a correlation calculated between the spectral information of the subject 10 and the spectral information of the plurality of materials stored in the database 110, and may analyze the spectral information of the subject 10 by comparing the reconstructed spectrum reconstructed from the result information and the spectral data stored in the database 110 with each other.

Figure 9:
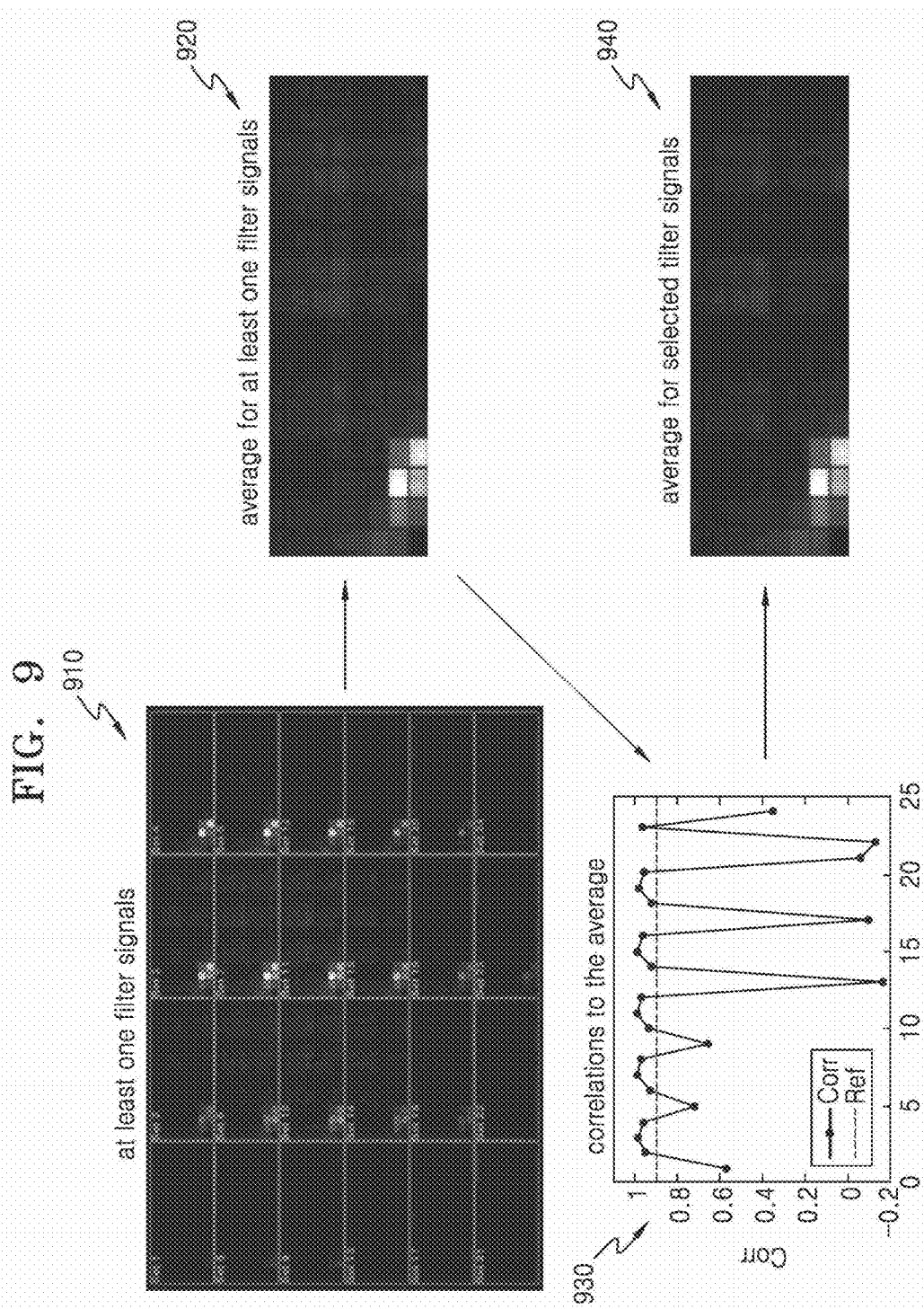
FIG. 9 is a diagram illustrating a process of generating spectral information of a subject, according to an exemplary embodiment.

FIG. 9 is a diagram illustrating a process of generating spectral information of a subject, according to an exemplary embodiment.

Referring to FIG. 9, the controller 130 may calculate an average filter signal 920 for a plurality of filter signals 910, calculate a second correlation between each of the plurality of filter signals 910 and the average filter signal 920, and generate the spectral information of the subject 10, based on the second correlation.

In the disclosure, the spectral information of the subject 10, the spectral information of the candidate materials, and the plurality of filter signals are described in a one-dimensional (1D) form such that the plurality of spectral channels 122 are located on a 1D horizontal axis and signal intensities corresponding to the plurality of spectral channels 122 are indicated on a vertical axis. Alternatively, the spectral information of the subject 10, the spectral information of the candidate materials, and the plurality of filter signals may be described in a two-dimensional (2D) form such that the plurality of spectral channels 122 are located on a 2D plane and the signal intensities corresponding to the plurality of spectral channels 122 are indicated with brightnesses corresponding thereto.

The 1D form and the 2D form each representing the spectral information of the subject 10, the spectral information of the candidate materials, and the plurality of filter signals are different only in terms of methods of expression, and the information represented by the two formats may be substantially the same. The plurality of filter signals 910 illustrated in FIG. 9 may be displayed two-dimensionally.

The controller 130 may generate the spectral information of the subject 10, based on the plurality of filter signals. For example, the controller 130 may generate the spectral information of the subject 10 by selecting at least one of the plurality of filter signals and calculating an average filter signal for the selected at least one filter signal. The controller 130 may select at least one of the plurality of filter signals in various methods. In an exemplary embodiment, the controller 130 may select at least one of the plurality of filter signals by using a correlation as illustrated in FIG. 9.

The controller 130 may calculate an average filter signal 920 for a plurality of filter signals 910. For example, when the plurality of spectral filters include 24 spectral filters, the controller 130 may generate 24 filter signals. The controller 130 may calculate the average filter signal 920 corresponding to an average of the 24 filter signals. The average filter signal 920 may represent the intensity of a signal of each of wavelength bands corresponding to the plurality of spectral channels 122, similar to the plurality of filter signals 910.

The controller 130 may calculate a second correlation between each of the plurality of filter signals 910 and the average filter signal 920. The second correlation may be understood as being substantially the same as the above-described first correlation. For example, when the plurality of spectral filters include 24 spectral filters, the controller 130 may calculate 24 second correlations. A graph 930 shows examples of second correlations between the 24 spectral filters and the average filter signal 920.

The controller 130 may generate the spectral information of the subject 10, based on the second correlation. For example, the controller 130 may generate the spectral information of the subject 10 by selecting signals each having a second correlation greater than a reference value from among the plurality of filter signals 910 and calculating an average signal for the signals each having the second correlation greater than the reference value.

In detail, when the plurality of spectral filters include 24 spectral filters, signals each having a correlation greater than the reference value among 24 second correlations may be selected. Referring to the graph 930, the controller 130 may select 16 signals each having a correlation greater than the reference value among the 24 second correlations. The controller 130 may generate the spectral information of the subject 10 by calculating an average signal 940 for the 16 signals each having the correlation greater than the reference value.

As the controller 130 generates the spectral information of the subject 10 based on the second correlation as described above, signals each having a correlation less than the reference value among the plurality of filter signals may be excluded in the generation of the spectral information of the subject 10. Thus, a signal-to-noise ratio (SNR) of the spectral information of the subject 10 may be increased and thus the quality of the spectral information of the subject 10 may be improved.

Figure 10:
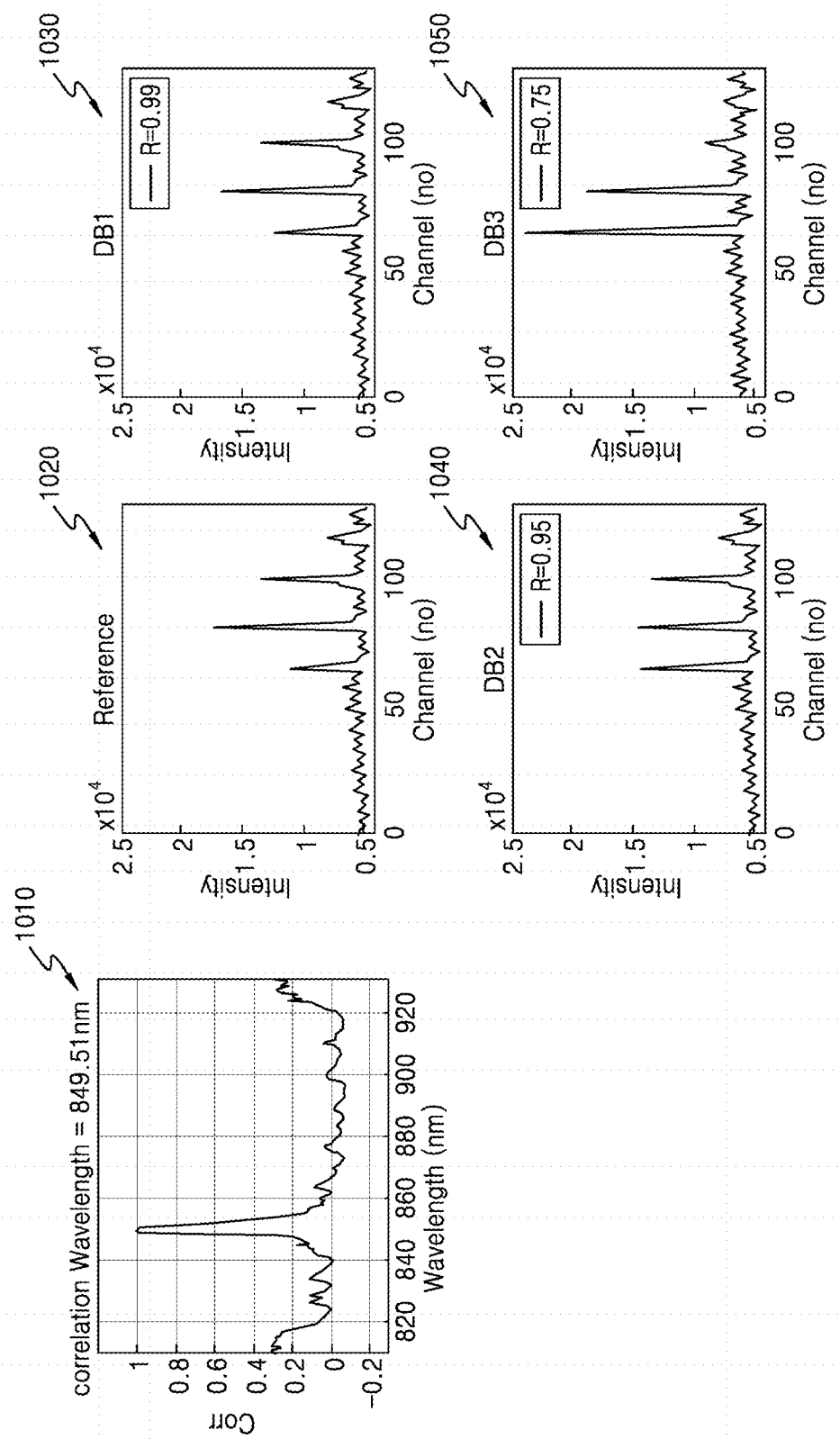
FIG. 10 is a diagram illustrating a correlation between a plurality of pieces of spectral information of an optical signal having a single wavelength, according to an exemplary embodiment.

FIG. 10 is a diagram illustrating a correlation between a plurality of pieces of spectral information of an optical signal having a single wavelength, according to an exemplary embodiment.

In FIG. 10, reference character "reference" in a graph 1020 denotes spectral information that is generated by the apparatus 100 from a laser signal having a single wavelength of 849.51 nm, and reference characters "DB1", "DB2", and "DB3" in graphs 1030, 1040, 1050 denote spectral information that are generated by the apparatus 100 from laser signals of different wavelength bands from 849.51 nm. A graph 1010 may show correlations between the spectral information reference and the spectral information DB1, DB2, DB3 regarding the laser signals of the other wavelength bands.

Referring to the graph 1010, the correlations between the spectral information reference and the spectral information DB1, DB2, DB3 regarding the laser signals of the other wavelength bands are 1 at a wavelength of 849.51 nm, and sharply decrease at wavelengths greater than or less than 849.51 nm.

Referring to the spectral information DB1, DB2, DB3 regarding the laser signals each having a wavelength close to 849.51 nm, the correlations thereof may be high when the intensities and channels of peaks are similar. In detail, a correlation is obtained as 0.99 with respect to the spectral information DB1 in the graph 1030, a correlation is obtained as 0.95 with respect to the spectral information DB2 in the graph 1040, and a correlation is obtained as 0.75 with respect to the spectral information DB1 in the graph 1050.

Figure 11A:
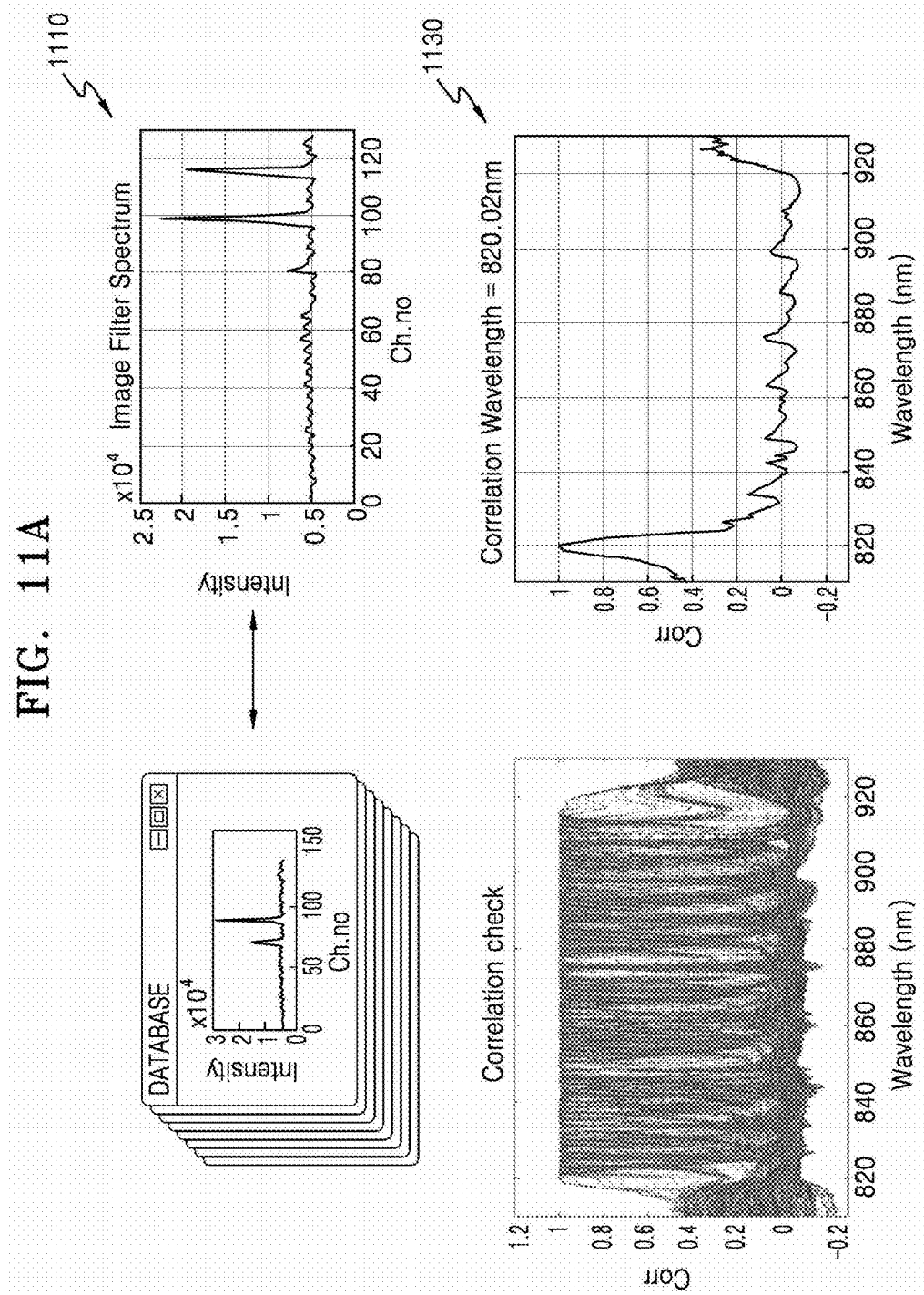
FIGS. 11A and 11B are diagrams comparing a one-dimensional (1D) correlation between two different pieces of spectral information and a two-dimensional (2D) correlation between the two different pieces of spectral information, according to an exemplary embodiment.
Figure 11B:
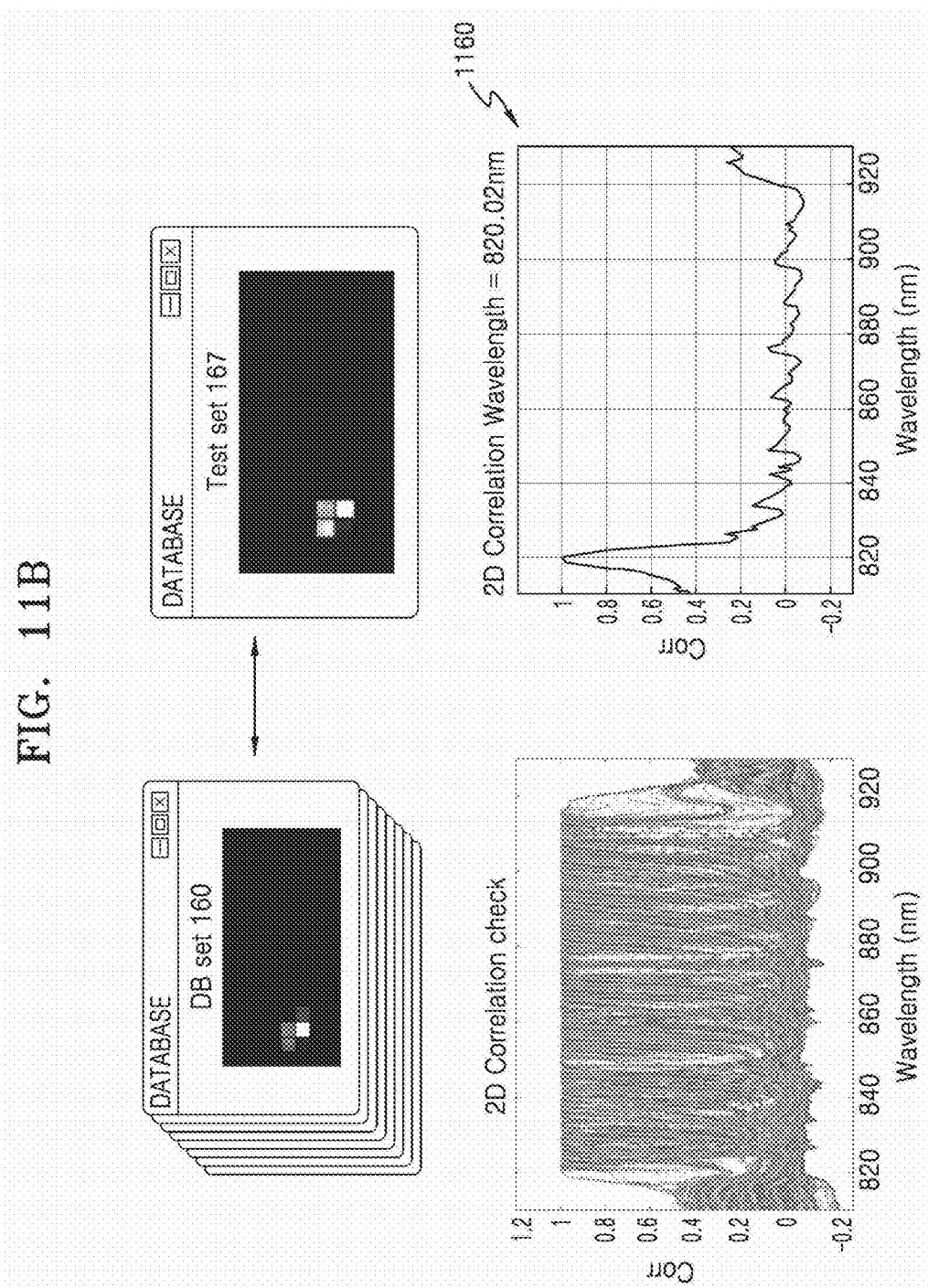

FIGS. 11A and 11B are diagrams comparing a 1D correlation between two different pieces of spectral information and a 2D correlation between the two different pieces of spectral information, according to an exemplary embodiment.

FIG. 11A illustrates a 1D correlation between two different pieces of spectral information. FIG. 11B illustrates a 2D correlation between the two different pieces of spectral information. In the disclosure, the term "a correlation" may be understood to mean a 1D correlation, unless a 2D correlation is specifically described.

The 1D correlation may be calculated based on 1D data shown in a graph 1110 representing the intensity of a wavelength band signal passing through each of the plurality of spectral channels 122. The 2D correlation may be calculated based on 2D information received by the image sensor 123 from the plurality of spectral channels 122.

A comparison between the 1D correlation as shown in a graph 1130 of FIG. 11A and the 2D correlation as shown in a graph 1160 of FIG. 11B reveals that there is no large difference therebetween. However, a time required to calculate the 1D correlation may be significantly less than a time required to calculate the 2D correlation. The difference between the 1D correlation and the 2D correlation is very small in terms of effects but is remarkably large in terms of a calculation time. Accordingly, the 1D correlation may be employed by the apparatus 100 for analyzing spectral information according to the disclosure, rather than the 2D correlation.

Figure 12:
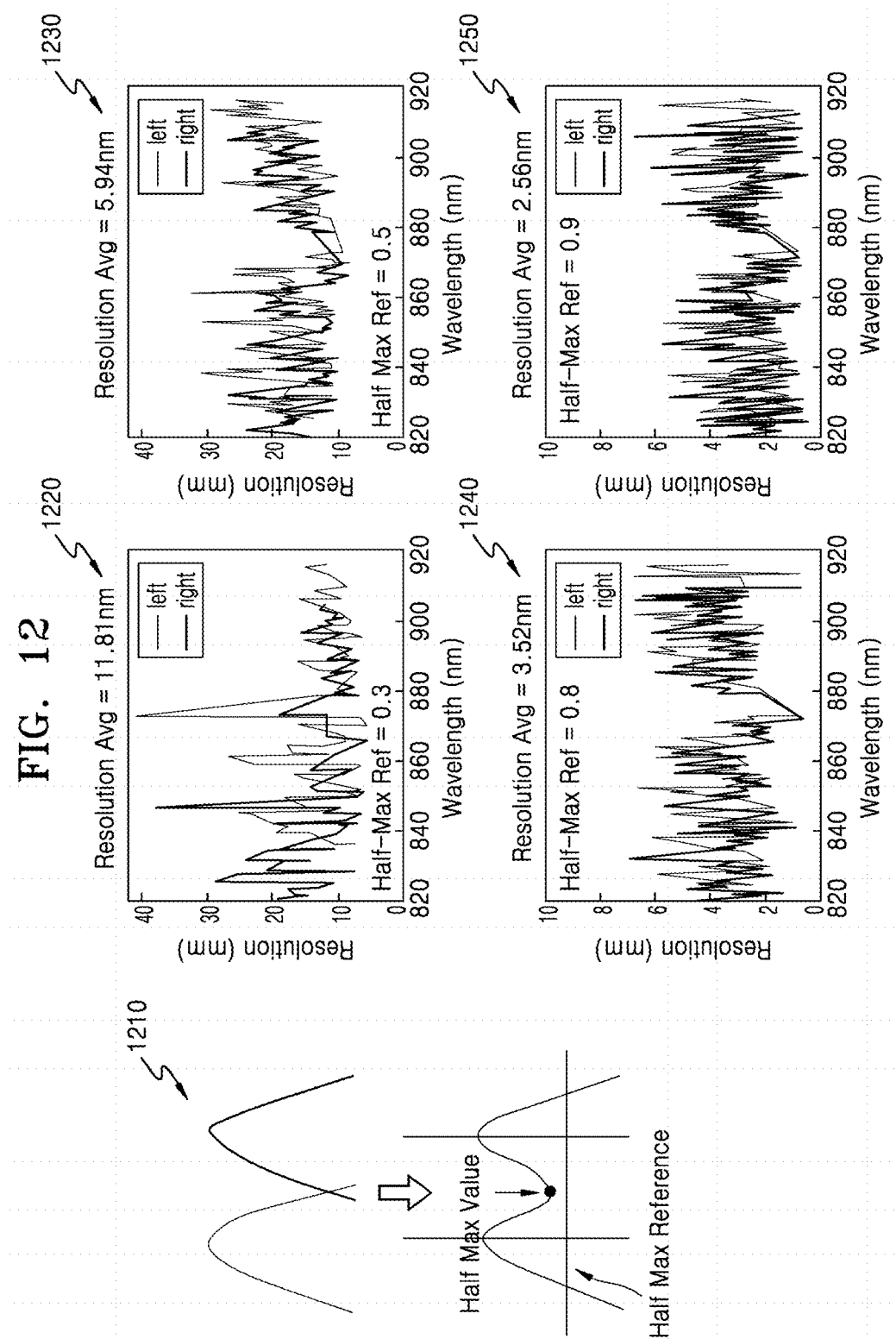
FIG. 12 is a diagram illustrating an example of measuring a resolution of an apparatus for analyzing spectral information, according to an exemplary embodiment.

FIG. 12 is a diagram illustrating an example of measuring a resolution of an apparatus for analyzing spectral information, according to an exemplary embodiment.

In FIG. 12, a graph 1210 shows a half-max value and a half-max reference that are used in measuring the resolution of the spectral information analyzing apparatus, and graphs 1220, 1230, 1240, and 1250 shows a result of measuring the resolution of the apparatus when a half-max reference value is changed.

The graph 1210 shows that a reconstructed spectrum of a laser signal having a single wavelength may have a peak, and also shows a method of measuring resolutions of two peaks of two reconstructed spectrums of two laser signals having different wavelengths (for example, a reconstructed spectrum shown as a normal line and a reconstructed spectrum shown as a bold line in the graph 1210). The two laser signals are not distinguishable from each other when a half-max value of the two peaks is greater than a half-max reference value, and are distinguishable from each other when the half-max value of the two peaks is less than a half-max reference value.

The resolution may be a threshold value at which the wavelengths of the two laser signals are distinguishable from each other. For example, the resolution of the apparatus 100 may be about 5 nm (or 5.94 nm as shown in the graph 1230), when the apparatus 100 is capable of distinguishing a reconstructed spectrum of an 815 nm laser signal from that of an 810 nm laser signal but cannot distinguish a reconstructed spectrum of an 814 nm laser signal from that of the 810 nm laser signal.

A result of measuring a resolution, when the half-max reference is 0.3, 0.5, 0.8 or 0.9, by the method of measuring the resolution of the apparatus 100 is shown in the graph 1220, 1230, 1240, or 1250. It may be understood that a resolution shown as a normal line in the graphs 1220-1250 corresponds to a resolution when a reference peak is on a right side (or a higher wavelength) and a measured peak is approaching from a left side (or a lower wavelength), and a resolution shown as a bold line in the graphs 1220-1250 corresponds to a resolution when a reference peak is on a left side (or a lower wavelength) and a measured peak is approaching from a right side (or a higher wavelength).

As the half-max reference value increases, two peaks are more distinguishable from each other and thus a value of the resolution decreases, thereby improving the spectroscopic performance of the apparatus 100.

Figure 13:
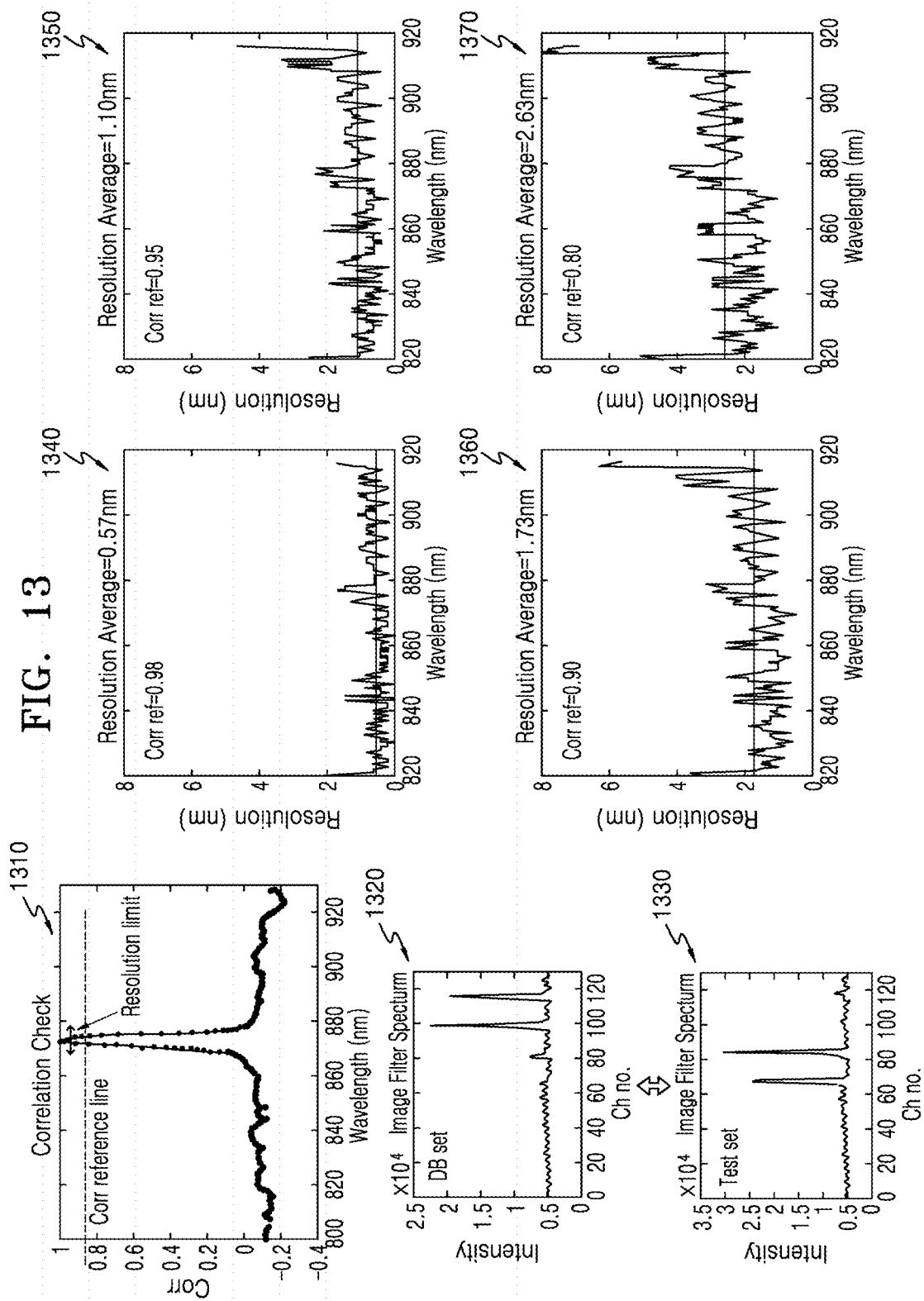
FIG. 13 is a diagram illustrating another example of measuring a resolution of an apparatus for analyzing spectral information, according to an exemplary embodiment.

FIG. 13 is a diagram illustrating another example of measuring a resolution of an apparatus for analyzing spectral information, according to an exemplary embodiment.

In FIG. 13, a graph 1310 shows a method of measuring a resolution by determining whether two laser signals as shown in a graph 1320 and a graph 1330 are distinguishable from each other, based on a correlation between spectral information of the two laser signals of the graphs 1320, 1330 having different wavelengths, and a graph 1320 shows a result of measuring the resolution when a reference correlation is changed.

Referring to the graph 1310, the resolution may be measured, based on a correlation between spectral information DB regarding laser signals having a plurality of wavelengths and spectral information target regarding a laser signal having a certain wavelength. It may be determined that the laser signals having the plurality of wavelengths and the laser signal having the wavelength are substantially the same and thus are not distinguishable from each other when the correlation between the spectral information target and the spectral information DB is greater than the reference correlation, and are different from each other and thus are distinguishable from each other when the correlation is not greater than the reference correlation.

The graphs 1340, 1350, 1360, and 1370 show respective results of measuring a resolution when reference correlations are 0.98, 0.95, 0.9, and 0.8. When a reference correlation is increased, the tendency that laser signals having adjacent wavelengths are determined to be not similar increases, and a value of the resolution decreases, thereby improving the performance of the apparatus 100.

FIGS. 12 and 13 illustrate methods of measuring a resolution of the apparatus 100 for analyzing spectral information according to exemplary embodiments of the disclosure. The apparatus 100 may be embodied as a system-on-chip to reduce a size and a weight thereof. According to the exemplary embodiments, while the size and the weight of the apparatus 100 are reduced, the apparatus 100 may have a low resolution. For example, the apparatus 100 may have a resolution of 3 nm or less by setting a parameter such as a median-maximum reference or a reference correlation. Accordingly, the apparatus 100 may distinguish a wavelength of 810 nm and a wavelength of 813 nm from each other, and have high performance despite a small size thereof.

FIG. 14 is a flowchart of a method of analyzing spectral information, according to an exemplary embodiment.

Referring to FIG. 14, a method of analyzing spectral information includes operations performed by the apparatus 100 illustrated FIG. 2. Thus, although not described below, the above description with respect to the apparatus 100 of FIG. 2 may also apply to the method of analyzing spectral information of FIG. 14. In an exemplary embodiment, operations described in FIG. 14 may be performed in a sequential manner, but a person skilled in the art should know that the disclosure is not limited to any described sequence of operations, as some operations can adopt other sequences or can be performed simultaneously depending on embodiments.

In operation 1410, the apparatus 100 may store spectral information of a plurality of materials. In detail, the apparatus 100 may store spectral information of, for example but not limited to, certain nutrients, a toxic material due to decay, blood glucose, etc. as a plurality of materials to be detected in relation to an application example.

In operation 1420, the apparatus 100 may generate spectral information of the subject 10 by filtering an optical signal from the subject 10 in units of wavelengths.

The apparatus 100 may filter the optical signal in units of wavelengths due to the plurality of spectral channels 122 that are set to pass different wavelength bands of the optical signal, and may generate spectral information of the subject 10, based on at least one filter signal. The at least one filter signal may represent the intensities of wavelength band signals passing through the plurality of spectral channels 122.

The apparatus 100 may calculate an average filter signal for the at least one filter signal, calculate a second correlation between each of the at least one filter signal and the average filter signal, and generate the spectral information of the subject 10, based on the second correlation.

The apparatus 100 may generate the spectral information of the subject 10 by selecting at least one signal having a second correlation greater than a reference value from among the at least one filter signal and calculating an average signal for the at least one signal having the second correlation greater than the reference value.

In operation 1430, the apparatus 100 may select candidate materials related to a certain application example from among the plurality of materials. In detail, the apparatus 100 may select candidate materials related to an application example, which is selected from among a plurality of application examples, from among the plurality of materials related to the stored spectral information.

In operation 1440, the apparatus 100 may calculate a first correlation between spectral information of each of the candidate materials and the spectral information of the subject 10. The apparatus 100 may calculate the first correlation based on the intensity of a wavelength-band signal for each piece of the spectral information.

In operation 1450, the apparatus 100 may generate result information based on the first correlation.

The apparatus 100 may select at least one final material having a first correlation greater than the reference value from among the candidate materials and generate result information regarding the at least one final material.

The result information may include information as to whether the at least one final material is detected from the subject 10, and the concentration of the at least one final material of the subject 10.

The apparatus 100 may adjust the reference value to improve the accuracy of the result information and select the at least one final material based on the adjusted reference value.

The apparatus 100 may emit light onto the subject 10. The optical signal may be generated from the light emitted onto the subject 100.

The application example may be to provide information regarding a chemical or physiological state of the subject 10 based on the spectral information of the subject 10.

A spectroscopic unit according to the disclosure employs the image sensor-based spectroscopic method and thus the size and/or the weight thereof may be reduced. While the size and/or the weight of the spectroscopic unit may be reduced, the high quality of result information generated by the spectroscopic unit as a correlation for information stored in a database is used by an apparatus for analyzing spectral information may be maintained.

The method of analyzing spectral information may be recorded on a computer-readable recording medium having recorded thereon one or more programs including instructions for executing the method. Examples of the computer-readable recording medium include magnetic media such as a hard disc, a floppy disk and a magnetic tape, optical media such as a CD-ROM and a DVD, magneto-optical media such as a floptical disk, and hardware devices such as ROM, RAM, flash memory, etc. which are specially configured to store and execute program instructions. Examples of the program instructions may include not only machine language code generated by a compiler but also high-level language code executable by a computer through an interpreter or the like.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above exemplary embodiments may be implemented in algorithms that execute on one or more processors. Furthermore, the components, elements or units represented by a block or processing operations may employ any number of related art techniques for electronics configuration, signal processing and/or control, data processing and the like.

While a few exemplary embodiments have been described above, the scope of the disclosure is not limited thereto and various modifications and improvements made by those of ordinary skill in the art to concepts defined in the following claims should be understood to fall within the scope of the disclosure.

What is claimed is:

1. An apparatus for analyzing spectral information, the apparatus comprising:
   a database configured to store spectral information of a plurality of materials analyzed by the apparatus;
   a spectroscope configured to generate spectral information of a subject by filtering an optical signal received from the subject in units of wavelengths; and
   a processor configured to obtain correlations between spectral information of each of candidate materials from among the plurality of materials and the spectral information of the subject, and generate result information based on the correlations,
wherein the spectroscope comprises:
at least one spectral filter configured to filter the optical signal in the units of wavelengths, the at least one spectral filter each including a plurality of spectral channels which are set to pass different wavelengths of the optical signal; and
an image sensor configured to generate the spectral information of the subject, based on at least one filter signal generated by the at least one spectral filter,
wherein the at least one filter signal represents intensities of wavelength band signals passing through the plurality of spectral channels, and
wherein the processor is further configured to obtain an average filter signal for the at least one filter signal, obtain second correlations between each of the at least one filter signal and the average filter signal, and generate the spectral information of the subject, based on the second correlations between each of the at least one filter signal and the average filter signal.

2. The apparatus of claim 1, wherein the processor is further configured to select at least one final material of which a correlation with the spectral information of the subject among the correlations is greater than a reference value from among the candidate materials and generate the result information regarding the at least one final material.

3. The apparatus of claim 2, wherein the result information comprises at least one of:
information indicating whether the at least one final material is detected from the subject; and
a concentration of the at least one final material in the subject.

4. The apparatus of claim 2, wherein the processor is further configured to adjust the reference value, and select the at least one final material based on the adjusted reference value.

5. The apparatus of claim 1, wherein the processor is further configured to select at least one filter signal of which a second correlation with the average filter signal among the second correlations is greater than a reference value from among the at least one filter signal and generate the spectral information of the subject based on an average signal for the at least one filter signal having the second correlation greater than the reference value.

6. The apparatus of claim 1, further comprising a light source configured to emit light onto the subject, and
wherein the optical signal is generated from the light emitted onto the subject.

7. The apparatus of claim 1, wherein the processor is further configured to select the candidate materials based on information regarding a chemical and/or physiological state of the subject.

8. The apparatus of claim 1, wherein the spectroscope is provided as a system-on-chip.

9. A computer-implemented method of analyzing spectral information, the method comprising:
storing spectral information of a plurality of materials;
generating spectral information of a subject by filtering an optical signal received from the subject in units of wavelengths;
obtaining correlations between spectral information of each of candidate materials from among the plurality of materials and the spectral information of the subject; and
generating result information based on the correlations,
wherein the generating the spectral information comprises:
filtering the optical signal in the units of wavelengths based on a plurality of spectral channels that are set to pass different wavelengths of the optical signal; and
generating the spectral information of the subject, based on at least one filter signal, and
wherein the at least one filter signal represents intensities of wavelength band signals passing through the plurality of spectral channels, and
wherein the generating the spectral information further comprises:
obtaining an average filter signal for the at least one filter signal;
obtaining second correlations between each of the at least one filter signal and the average filter signal; and
generating the spectral information of the subject, based on the second correlations between each of the at least one filter signal and the average filter signal.

10. The method of claim 9, wherein the generating the result information comprises:
selecting at least one final material of which a correlation with the spectral information of the subject among the correlations is greater than a reference value from among the candidate materials; and
generating the result information regarding the at least one final material.

11. The method of claim 10, wherein the result information comprises at least one of:
information indicating whether the at least one final material is detected from the subject; and
a concentration of the at least one final material in the subject.

12. The method of claim 10, further comprising adjusting the reference value and selecting the at least one final material based on the adjusted reference value.

13. The method of claim 9, wherein the generating the spectral information of the subject based on the second correlations comprises:
selecting at least one filter signal of which a second correlation with the average filter signal among the second correlations is greater than a reference value from among the at least one filter signal; and
generating the spectral information of the subject based on an average signal for the at least one filter signal having the second correlation greater than the reference value.

14. The method of claim 9, further comprising emitting light onto the subject, and
wherein the optical signal is generated from the light emitted onto the subject.

15. The method of claim 9, wherein the selecting comprises selecting the candidate materials based on information regarding a chemical and/or physiological state of the subject.

16. A non-transitory computer-readable recording medium having recorded thereon a program, which, when executed by at least one processor, causes the at least one processor to perform a method of analyzing spectral information, the method comprising:
storing spectral information of a plurality of materials;
generating spectral information of a subject by filtering an optical signal received from the subject in units of wavelengths;

obtaining correlations between spectral information of each of candidate materials from among the plurality of materials and the spectral information of the subject; and generating result information based on the correlations, wherein the generating the spectral information comprises:
   filtering the optical signal in the units of wavelengths based on a plurality of spectral channels that are set to pass different wavelengths of the optical signal; and
   generating the spectral information of the subject, based on at least one filter signal, and wherein the at least one filter signal represents intensities of wavelength band signals passing through the plurality of spectral channels, and wherein the generating the spectral information further comprises:
   obtaining an average filter signal for the at least one filter signal;
   obtaining second correlations between each of the at least one filter signal and the average filter signal; and
   generating the spectral information of the subject, based on the second correlations between each of the at least one filter signal and the average filter signal.

* * * * *